United States Patent
Kuwabara

[11] Patent Number: 5,832,054
[45] Date of Patent: Nov. 3, 1998

[54] FLUORESCENT X-RAY ANALYZER WITH QUICKLY EVACUABLE COVER CASES

[75] Inventor: Shoji Kuwabara, Osaka, Japan

[73] Assignee: Shimadzu Corporation, Kyoto, Japan

[21] Appl. No.: 912,892

[22] Filed: Aug. 15, 1997

[30] Foreign Application Priority Data

Nov. 29, 1996 [JP] Japan .................................. 8-319275

[51] Int. Cl.$^6$ ................................................. G01N 23/223
[52] U.S. Cl. ................................................. 378/45; 378/80
[58] Field of Search .................................. 378/44–50, 80

[56] References Cited

U.S. PATENT DOCUMENTS 4,720,842  1/1988  Kira et al. ................................. 378/45

*Primary Examiner*—Craig E. Church
*Attorney, Agent, or Firm*—Majestic, Parsons, Siebert & Hsue P.C.

[57] ABSTRACT

A fluorescent x-ray analyzer of the type irradiating a sample from below is provided with both a larger outer cover case and a smaller outer cover case respectively for covering a relatively large and small sample placed on top of a base plate at the top of an evacuable analysis chamber. The inner cover case is attached to the inside of the outer cover case when a small sample is to be analyzed but the two cover cases are separated and only the outer cover case is used when a larger sample is to be analyzed such that only a small amount of air is required to be removed to create a vacuum environment around the sample. Two air routes are formed through the base plate, an inner one being inside the inner cover case and the outer one being outside the inner cover case but inside the outer cover case when the inner cover case is used attached to the outer cover case such that a vacuum pump connected to the analysis chamber and through a valve to the outer air route can be activated to selectively evacuate either the interior of the inner cover case if the two cover cases are attached to each other or the interior of the outer cover case if the inner cover case is detached therefrom. Alternatively, the outer and inner cover cases may be provided respectively with a discharge pipe connected to a vacuum pump and a discharge air route which can be connected to the discharge pipe when the two cover cases are attached to each other.

8 Claims, 3 Drawing Sheets

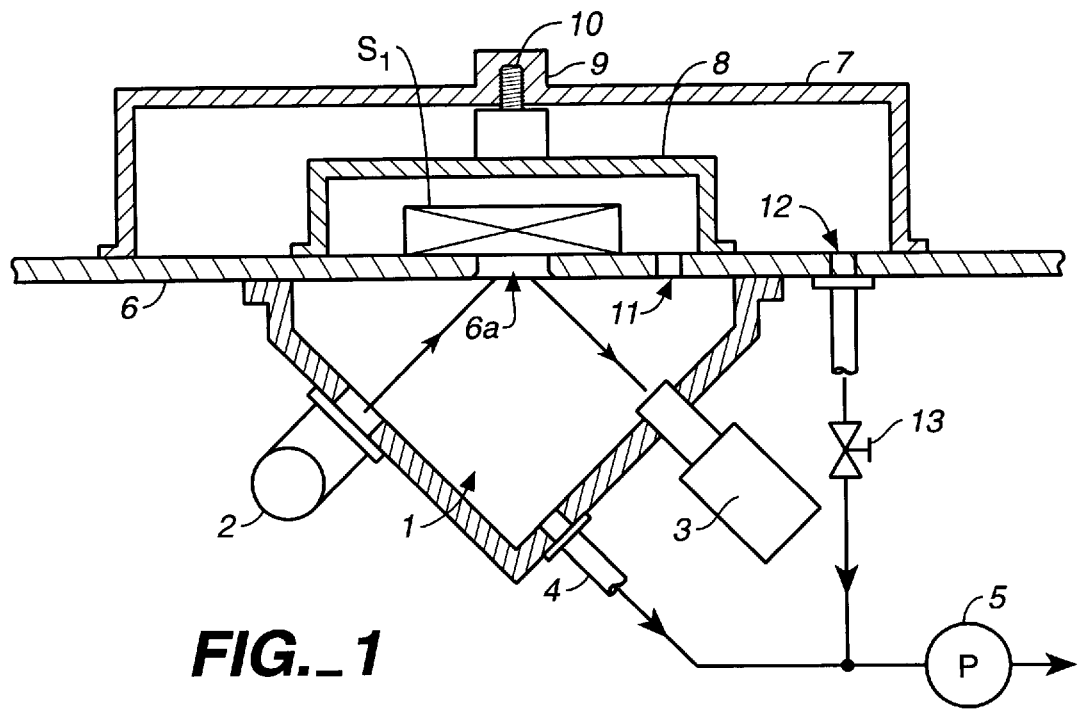
FIG._1
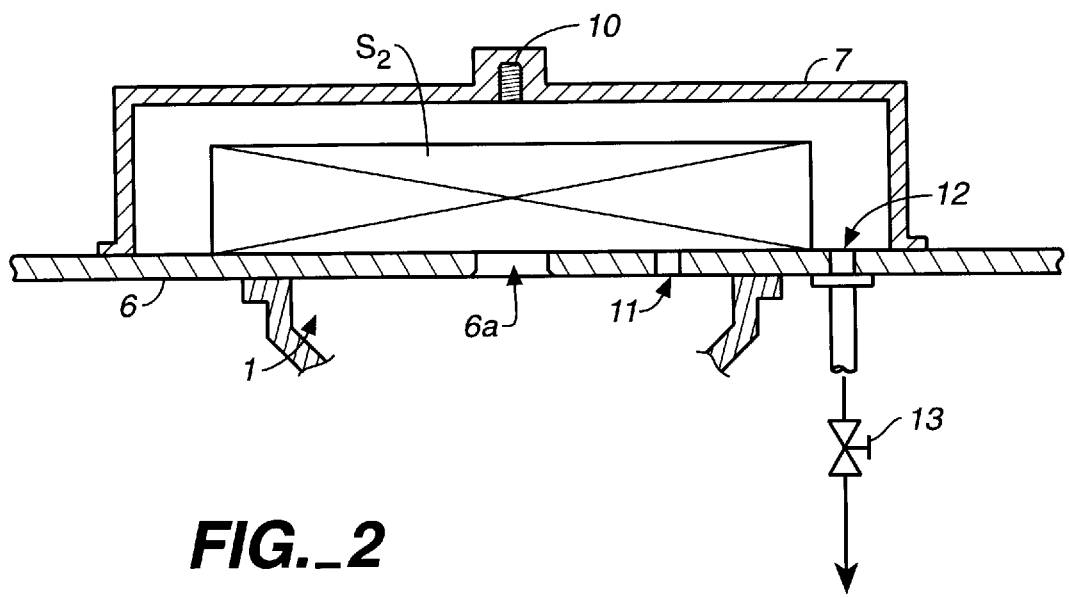
FIG._2

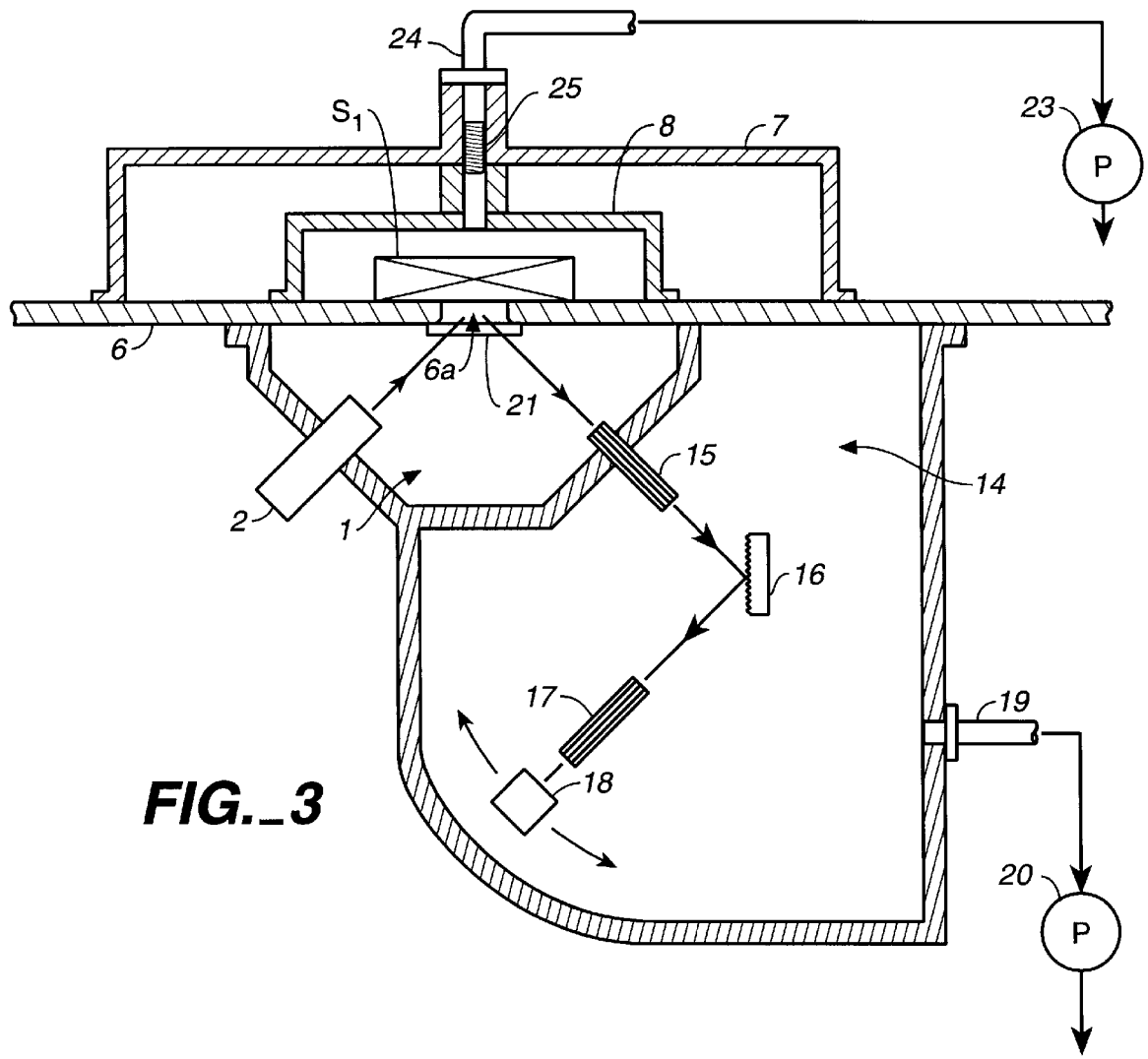
FIG._3
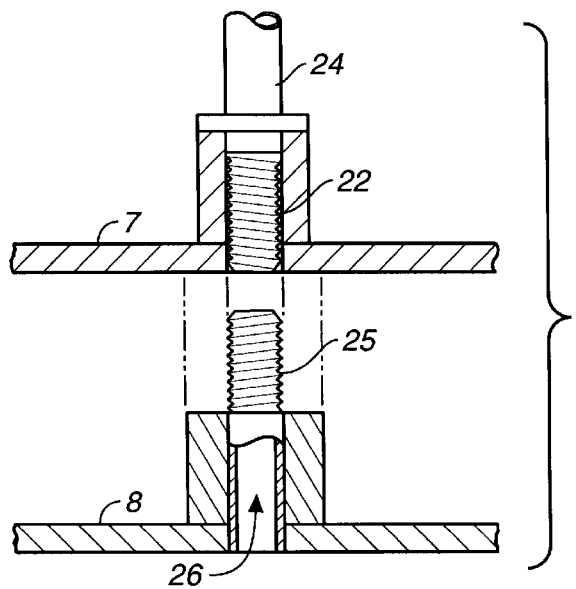
FIG._4

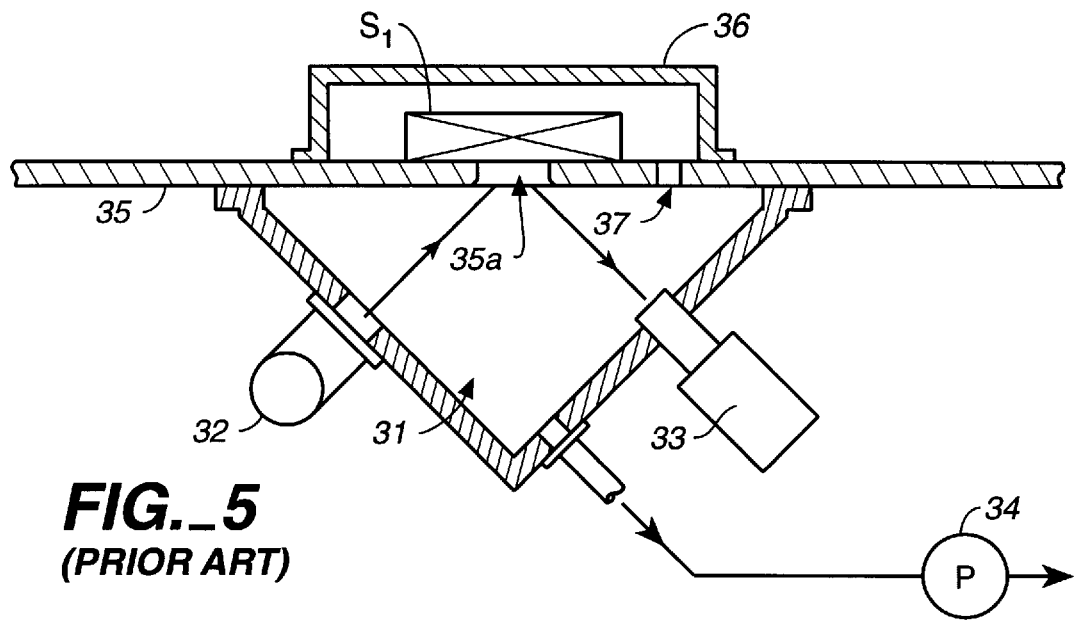
FIG._5
(PRIOR ART)
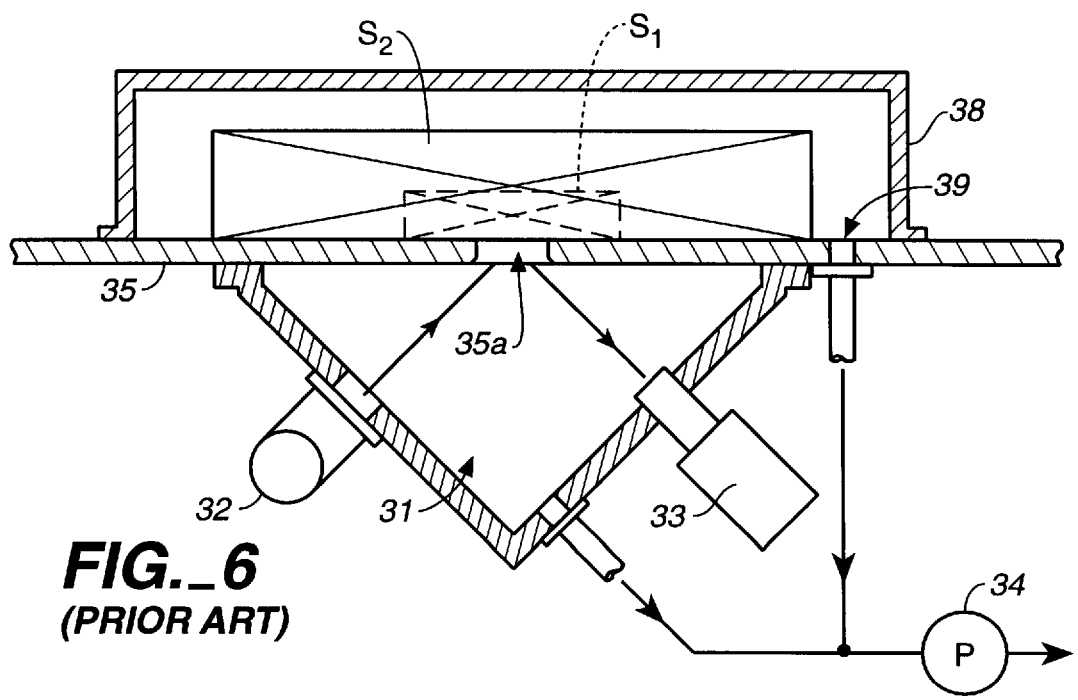
FIG._6
(PRIOR ART)

5,832,054

FLUORESCENT X-RAY ANALYZER WITH QUICKLY EVACUABLE COVER CASES

BACKGROUND OF THE INVENTION

This invention relates to a fluorescent x-ray analyzer of the type adapted to irradiate a sample from below with excitation x-rays and to detect fluorescent x-rays on the lower side of the sample. The invention relates more particularly to the part of such an analyzer where samples are set.

Fluorescent x-ray analyzers can be roughly divided into the upper-surface irradiating type adapted to expose the upper surface of a sample to the exciting x-rays and the lower-surface irradiating type adapted to expose the lower surface of a sample to the exciting x-rays. A mechanism for pushing up the sample to the height of irradiation is required for an analyzer of the former type, but the sample needs only to be placed at the position of x-ray irradiation in the case of an analyzer of the latter type and hence only a simple structure is necessary for setting the sample.

FIG. 5 shows schematically the structure of a prior art fluorescent x-ray analyzer of an energy-dispersing type as an example of the lower-surface irradiating type. An x-ray source 32 and a detector 33 are attached facing upward to the outer wall at lower parts of an evacuable chamber 31. The detector 33 is for detecting x-rays over an entire range of wavelength and is adapted to take in all wavelength components of the fluorescent x-rays without dispersing them. Since the elements contained in air, if found inside the chamber 31, absorb portions of the x-rays and adversely affect the results of analysis, a vacuum pump 34 may be used to provide a vacuum environment inside the chamber 31, or the interior of this chamber 31 may be filled with a helium gas.

A sample-setting position is defined above this evacuable chamber 31. A base plate 35 for placing a sample (indicated by symbol $S_1$ in FIG. 5) thereon is placed above the chamber 31, having a small window 35a at its center to allow x-rays to pass through. If the sample $S_1$ is relatively small, a hermetically sealable cover case 36 of a correspondingly small size may be provided to cover the sample $S_1$. The base plate 35 is further provided with a discharge air route 37 at a position inside the cover case 36 such that the air inside the cover case 36 can be removed therethrough as the chamber 31 is evacuated.

FIG. 6 shows another prior art fluorescent x-ray analyzer which is adapted for use with a relatively large sample $S_2$, provided with an accordingly larger hermetically sealable cover case 38. An air route 39 is provided to its base plate 35 at a position inside the cover case 38 far enough from the center so as not to be blocked by the sample $S_2$ and to allow the air inside the cover case 38 to be removed therethrough.

If a fluorescent x-ray analyzer structured as shown in FIG. 5, for a relatively small sample, is used to analyze a relatively large sample, the sample may not fit inside the smaller cover case 36 and/or the air route 37 may be blocked by the sample. A fluorescent x-ray analyzer structured as shown in FIG. 6, for a relatively large sample, on the other hand, can also be used for a smaller sample. It may therefore be suggested that the sample-setting parts of all fluorescent x-ray analyzers should be structured as shown in FIG. 6 to be able to accommodate both relatively small and large samples. This, however, is not a practical solution to the problem.

If, for example, a relatively small sample (such as indicated by symbol $S_1$) is set on an analyzer suited for the analysis of a larger sample (such as shown in FIG. 6), there is left inside the cover case 38 a relatively large empty space. As explained above, however, the air inside the cover case 38 must be removed. A large space inside the cover case 38 containing a small sample $S_1$ therein means that it takes a longer time to create a vacuum environment. When a large number of samples must be analyzed, the loss of time caused by the removal of extra air is not negligible, and it definitely affects the overall efficiency of the analysis.

SUMMARY OF THE INVENTION

It is therefore an object of this invention in view of this problem of prior art technology to provide an improved fluorescent x-ray analyzer capable of analyzing both smaller and larger samples efficiently without incurring an unreasonable time loss in the evacuation of the interior of its cover case.

A fluorescent x-ray analyzer embodying this invention, with which the above and other objects can be accomplished, may be characterized as comprising a larger outer cover case suitable for a relatively large sample and a smaller inner cover case suitable for a relatively small sample. These two cover cases can be attached one inside the other or may be detached from each other to cover a sample placed on top of a base plate above an evacuable chamber and to create therein a vacuum condition. Two air routes are formed through the base plate, an inner one being inside the inner cover case and the outer one being outside the inner cover case but inside the outer cover case when the inner cover case is used attached to the outer cover case such that a vacuum pump connected to the evacuable chamber and through a valve to the outer air route can be activated to selectively evacuate either the interior of the inner cover case if the two cover cases are attached to each other or the interior of the outer cover case if the outer cover case is used with the inner cover case detached therefrom.

Alternatively, the outer and inner cover cases may be provided respectively with a discharge pipe connected to a vacuum pump and a discharge air route which can be connected to the discharge pipe when the two cover cases are attached to each other.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a vertical sectional view of a fluorescent x-ray analyzer according to a first embodiment of this invention when a relatively small sample is to be analyzed;

FIG. 2 is a vertical sectional view of a portion of the fluorescent x-ray analyzer of FIG. 1 when a relatively large sample is to be analyzed;

FIG. 3 is a vertical sectional view of another fluorescent x-ray analyzer according to a second embodiment of this invention when a relatively small sample is to be analyzed;

FIG. 4 is a vertical sectional view of a portion of the fluorescent x-ray analyzer of FIG. 2 where its inner and outer cover cases are attached and detached;

FIG. 5 is a vertical sectional view of a prior art fluorescent x-ray analyzer; and FIG. 6 is a vertical sectional view of another prior art fluorescent x-ray analyzer.

Throughout herein, like components are indicated by like numerals even where they are components of different analyzers, and their descriptions may not necessarily be given repetitiously for the sake of simplicity of explanation.

DETAILED DESCRIPTION OF THE INVENTION

FIGS. 1 and 2 show a fluorescent x-ray analyzer of the lower-surface irradiating and energy-dispersing type embodying this invention when a relatively small sample $S_1$ and a relatively large sample $S_2$ are set to be analyzed, respectively. The analyzer comprises an x-ray source 2 and a detector 3 adapted to take in all wavelength components of the fluorescent x-rays, both being attached, facing upward, to the outer wall on lower parts of a hermetically sealed evacuable chamber (herein referred to as the analysis chamber 1). A discharge pipe 4 is connected to this analysis chamber 1 such that the analysis chamber 1 can be evacuated by means of a vacuum pump 5. The upper surface of the analysis chamber 1 comprises a base plate 6 for having a sample S (either $S_1$ or $S_2$) placed thereon, with a window 6a formed at its center for passing x-rays therethrough.

The sample S to be analyzed is placed on this base plate 6 in a hermetically sealed condition. According to this embodiment of the invention, not only is there provided a larger outer cover case 7 for containing therein a relatively large sample $S_2$, but a smaller inner cover case 8, with a smaller internal volume than the outer cover case 7 and hence suitable for containing therein a relatively small sample $S_1$, is detachably attached inside the outer cover case 7.

Any appropriate mechanism may be employed for detachably attaching the inner and outer cover cases 8 and 7. According to the embodiment shown in FIGS. 1 and 2, this mechanism includes a male screw part 9 protruding outwardly from the top outer surface of the inner cover case 8 and a matching female screw part 10, engageable with the male screw part 9, formed on the inner surface of the top plate of the outer cover case 7 such that the inner and outer cover cases 8 and 7 can be attached to and detached from each other.

The base plate 6 is further provided with two air routes (an inner air route 11 and an outer air route 12) therethrough, leading respectively to the interior of the inner cover case 8 when the inner cover case 8 is attached to the outer cover case 7 and to the interior of the outer cover case 7 when the inner cover case 8 is detached therefrom. In other words, the air inside the inner cover case 8 can be removed through the inner air route 11 into the analysis chamber 1. The outer air route 12 is formed through the base plate 6 such that the space between the inner and outer cover cases 8 and 7 is connected therethrough to the analysis chamber 1. The outer air route 12 is connected to the vacuum pump 5 through a valve 13 which can be closed or opened.

When a relatively small sample $S_1$ is analyzed, it is placed at the center on the base plate 6 and is covered by the inner cover case 8 which is attached to the outer cover case 7 as shown in FIG. 1 such that the interior of the inner cover case 8 is in an air-communicating relationship through the inner air route 11 with the analysis chamber 1. Thereafter, the vacuum pump 5 is activated to evacuate the analysis chamber 1 with the outer air route 12 blocked by means of the valve 13. Since the analysis chamber 1 is in the air-communicating relationship with the interior of the inner cover case 8, the air inside the inner cover case 8 is also removed therefrom through the analysis chamber 1. In other words, a vacuum condition is established inside both the analysis chamber 1 and the inner cover case 8 such that an analysis can be carried out without the effect of absorption by air. Since the vacuum condition inside the inner cover case 8 can be established in this case merely by removing the relatively small amount of air between the inner wall of the inner cover case 8 and the outer surface of the sample $S_1$, the evacuation of air can be carried out extremely quickly.

When a relatively large sample $S_2$ is to be analyzed, it is placed at the center on the base plate 6 and is covered by the outer cover case 7 with the inner cover case 8 removed therefrom as shown in FIG. 2 such that the interior of the outer cover case 7 is in an air-communicating relationship through the outer air route 12 with the analysis chamber 1. Thereafter, the vacuum pump 5 is activated with the outer air route 12 connected thereto by opening the valve 13 such that the air inside the analysis chamber is discharged through the discharge pipe 4 and the air inside the outer cover case 7 is discharge through the outer air route 12. As a result, a vacuum condition is established inside both the analysis chamber 1 and the outer cover case 7 with the sample $S_2$ placed therein such that a fluorescent x-ray analysis can be carried out.

FIGS. 3 and 4 show another fluorescent x-ray analyzer of the lower-surface irradiating and wavelength-dispersing type embodying this invention with like components indicated by like numerals as in FIGS. 1 and 2. A detection chamber 14 is provided adjacent to the analysis chamber 1, and an x-ray source 2 is attached, facing upward, to the outer wall on a lower part of the analysis chamber 1. An entrance slit 15 is provided to the partition wall between the analysis chamber 1 and the detection chamber 14, and the detection chamber 14 contains therein a dispersing element 16 such as a diffraction grating for dispersing x-rays made incident thereon-through the entrance slit 15, an exit slit 17 for passing the x-rays dispersed by the dispersing element 16, and an x-ray detector 18 for analyzing the x-rays passed through the exit slit 17. A discharge pipe 19 is connected to this detection chamber 14 such that the air is continuously discharged from the interior of the analysis chamber 1 and the detection chamber 14 by means of a vacuum pump 20. A base plate 6 for holding a sample thereon is placed at the top of the analysis chamber 1 so as to hermetically seal the upper surface part of the analysis chamber 1. A shutter 21 is provided to a window 6a at the center of the base plate 6.

This analyzer, too, is provided with a larger outer cover case 7 for a relatively large sample and a smaller inner cover case 8 for a relatively small sample and detachably attachable to the inner side of the outer cover case 7.

The detachably attaching mechanism for the inner and outer cover cases 8 and 7 is better shown in FIG. 4, making use of hollow screws and their inner hollow parts serving as a disconnectably connectable air-discharging passageway. Explained more in detail with reference to FIG. 4, a vertically penetrating tubular female screw 22 is formed at the center of the upper plate of the outer cover case 7, and its outer opening is connected to a discharge pipe 24 leading to a vacuum pump 23 (shown in FIG. 3). A tubular male screw 25, engageable with the tubular female screw 22 from below, is formed, protruding upward from the center of the upper plate of the inner cover case 8. The hollow interior 26 of this tubular male screw 25 serves as a part of the air-discharging passage, penetrating the upper plate of the inner cover case 8.

When a relatively small sample $S_1$ is to be analyzed, it is set on top of the base plate 6 and covered with the inner cover case 8 to which is attached the outer cover case 7, as shown in FIG. 3. When a relatively large sample $S_2$ is to be analyzed, it is set on top of the base plate 6 and covered with the outer cover case 7 having the inner cover case 8 removed therefrom. In the former situation, the inner and outer cover cases 8 and 7 are attached together with the interior of the inner cover case 8 connected to the discharge pipe 24 through the tubular female and male screws 22 and 25 such that the air inside the inner cover case 8 can be removed through the discharge pipe 24. Since only the relatively small amount of air between the inner surface of the inner cover case 8 and the outer surface of the sample $S_1$ is required to be discharged, it is possible to complete the evacuation operation quickly. In the latter situation, the interior of the outer cover case 7 is connected to the discharge pipe 24 through the tubular female screw 22 such that the air inside the outer cover case 7 can be removed again through this discharge pipe 4.

In summary, the present invention provides fluorescent x-ray analyzers capable of analyzing both smaller and larger samples by placing them at the same place and irradiating them from below and providing a vacuum condition around the sample equally quickly whether the sample is relatively large and is covered with a larger cover case or it is relatively small and is covered with a smaller cover case.

What is claimed is:

1. A fluorescent x-ray analyzer comprising:

an evacuable analysis chamber covered with a base plate for placing a sample thereon;

means for irradiating said sample with x-rays from below;

a larger cover case for enclosing therein a relatively large sample placed on said base plate; and a smaller cover case for enclosing therein a relatively small sample placed on said base plate, said smaller cover case being detachably attachable inside and to said larger cover case, said base plate having an inner air route and an outer air route formed therethrough, said inner air route opening inside said smaller cover case, said outer air route opening between said larger cover case and said smaller cover case when said larger cover case and said smaller cover case are attached.

2. The fluorescent x-ray analyzer of claim 1 further comprising evacuating means for drawing air selectively from said analysis chamber or through said outer air route.

3. The fluorescent x-ray analyzer of claim 2 wherein said evacuating means include a vacuum pump connected both to said analysis chamber and through a valve to said outer air route.

4. A fluorescent x-ray analyzer comprising:

an evacuable analysis chamber covered with a base plate for placing a sample thereon;

means for irradiating said sample with x-rays from below;

a larger outer cover case for enclosing therein a relatively large sample placed on said base plate; and a smaller inner cover case for enclosing therein a relatively small sample placed on said base plate, said inner cover case being detachably attachable inside and to said outer cover case, a discharge pipe being connected to said outer cover case for removing air inside said outer cover case therethrough, said inner cover case having a discharge air passage which becomes connected to said discharge pipe when said inner cover case and said outer cover case are connected together.

5. The fluorescent x-ray analyzer of claim 4 further comprising evacuating means for drawing air selectively either from inside said inner cover case if said inner cover case and said outer cover case are connected or from inside said outer cover case if said inner cover case is detached from said outer cover case.

6. The fluorescent x-ray analyzer of claim 5 wherein said evacuating means include a vacuum pump connected to said discharge pipe.

7. The fluorescent x-ray analyzer of claim 4 wherein said outer cover case includes a tubular female screw connected to said discharge pipe and wherein said inner cover case includes a tubular male screw which can engage with said tubular female screw and serves as said discharge air passage.

8. The fluorescent x-ray analyzer of claim 4 further comprising an evacuable detection chamber which is adjacent to said analysis chamber, an entrance slit on a partition wall between said analysis chamber and said detection chamber and means for evacuating said detection chamber and said analysis chamber, said detection chamber containing therein a dispersing element for dispersing x-rays from said entrance slit, an exit slit for passing dispersed x-rays from said dispersing element, and an x-ray detector for detecting x-rays passed through said exit slit.

* * * * *